United States Patent [19]

Carr et al.

[11] Patent Number: 4,874,777

[45] Date of Patent: Oct. 17, 1989

[54] LEUKOTRIENE ANTAGONISTS

[75] Inventors: F. Patrick Carr, Indianapolis; Robert D. Dillard, Zionsville; Doris E. McCullough, Carmel, all of Ind.

[73] Assignee: Eli Lilly and Company, Indianapolis, Ind.

[21] Appl. No.: 37,284

[22] Filed: Apr. 10, 1987

[51] Int. Cl.[4] .................. C07D 257/04; A61K 31/41; A61K 31/05; C07C 39/02

[52] U.S. Cl. ..................... 514/381; 514/520; 514/521; 548/253; 562/426; 562/429; 562/431

[58] Field of Search ............... 548/253; 514/381, 571, 514/570; 562/463, 426, 425

[56] References Cited

U.S. PATENT DOCUMENTS

| | | | |
|---|---|---|---|
| 3,899,513 | 8/1975 | Warren et al. | 260/345.2 |
| 4,281,008 | 7/1981 | Chamberlain et al. | 424/269 |
| 4,424,231 | 1/1984 | Bantick et al. | 424/274 |
| 4,474,788 | 10/1984 | Bantick | 424/258 |
| 4,499,299 | 2/1985 | Bernstein et al. | 514/570 |
| 4,567,279 | 1/1986 | Chan | 548/491 |
| 4,617,407 | 10/1986 | Young et al. | 549/462 |
| 4,628,115 | 12/1986 | Carson et al. | 562/464 |
| 4,644,071 | 2/1987 | Masatern et al. | 549/417 |
| 4,650,812 | 3/1987 | Cohen et al. | 514/456 |

FOREIGN PATENT DOCUMENTS

| | | |
|---|---|---|
| 28063 | 5/1981 | European Pat. Off. . |
| 56172 | 7/1982 | European Pat. Off. . |
| 108592 | 5/1984 | European Pat. Off. . |
| 132366 | 1/1985 | European Pat. Off. . |

OTHER PUBLICATIONS

Derwent 86-219907/34 Abstracting EPO 191,401.
Dillard et al., *J. Med. Chem.*, 30(5), 911 (1987).

*Primary Examiner*—David B. Springer
*Attorney, Agent, or Firm*—Robert A. Conrad; Leroy Whitaker

[57] ABSTRACT

This invention provides benzene derivatives which are leukotriene antagonists, formulations of those derivatives, and a method of using those derivatives for the treatment of conditions characterized by an excessive release of leukotrienes.

20 Claims, No Drawings

LEUKOTRIENE ANTAGONISTS

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

It is the object of this invention to provide novel chemical agents which are selective leukotriene antagonists that can be used therapeutically in the treatment of allergic disorders such as asthma, where leukotrienes are thought to be causal mediators.

SUMMARY OF THE INVENTION

This invention provides for compounds of the Formula I

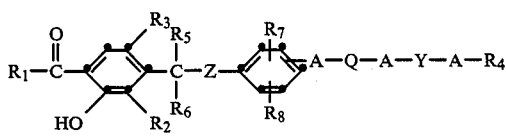

and pharmaceutically acceptable salts thereof, wherein:

$R_1$ is hydrogen, $C_1$-$C_6$ alkyl, $C_3$-$C_8$ cycloalkyl, phenyl-substituted-($C_1$-$C_3$ alkyl), phenyl, or phenyl substituted with a halo, $C_1$-$C_4$ alkyl, or $C_1$-$C_4$ alkoxy functionality;

$R_2$ is $C_1$-$C_{10}$ alkyl, $C_2$-$C_6$ alkenyl, benzyl, or 2-phenylethyl;

$R_3$ is hydrogen, bromo, chloro, $C_1$-$C_3$ alkyl, nitro, or —NRR;

Z is

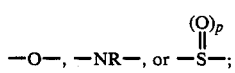

each A is a bond or a straight or branched chain $C_1$-$C_{10}$ alkylidene, $C_5$-$C_{10}$ cyclic alkylidene, or $C_2$-$C_4$ alkenylidene group;

Q is

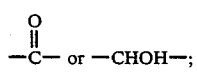

Y is

or a bond; or —A—Q—A—Y—, when taken together with two adjacent carbon atoms of the phenyl ring to which A is attached, is

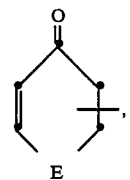

where E is a bond, —$CH_2$—, —S—, or —O—; and
$R_4$ is —$COR_9$, 5-tetrazolyl, 3-(1,2,5-thiadiazolyl), or 2-thioxo-4-thiazolidinonyl,
where R is hydrogen or $C_1$-$C_3$ alkyl;
each $R_5$ and $R_6$ is independently hydrogen, $C_1$-$C_3$ alkyl, phenyl, or benzyl;
each of $R_7$ an $R_8$ is independently hydrogen, $C_1$-$C_3$ alkoxy, halo, amino, hydroxy, or $C_1$-$C_3$ alkyl; and
$R_9$ is hydroxy or $C_1$-$C_4$ alkoxy; provided that
(a) all three A groups may not be a bond at the same time; and
(b) when Y is a group other than a bond, the A group between Q and Y may not be a bond.

Further provided by this invention is a method for treating immediate hypersensitivity conditions such as asthma, using compounds of Formula I above and pharmaceutical formulations containing these compounds.

DETAILED DESCRIPTION AND PREFERRED EMBODIMENT

The present invention relates to new organic compounds that are useful in the treatment of immediate hypersensitivity reactions. A preferred group of compounds are the compounds of Formula I wherein:

(a) $R_1$ is $C_1$-$C_6$ alkyl, especially methyl,
(b) $R_2$ is $C_1$-$C_6$ alkyl, especially ethyl and propyl,
(c) $R_3$ is hydrogen,
(d) $R_5$ is hydrogen,
(e) $R_6$ is hydrogen,
(f) Z is

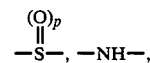

or especially —O—,
(g) $R_7$ and $R_8$ are each hydrogen, and
(h) Q is

and
(i) R is —COOH or 5-tetrazolyl.

An especially preferred group of compounds are those of Formula Ia:

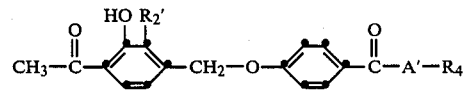

and pharmaceutically acceptable salts thereof wherein:
$R_2'$ is $C_1$-$C_6$ alkyl, especially ethyl or propyl;
A' is straight or branched chain $C_1$-$C_6$ alkylidene; and
$R_4'$ is —COOH or 5-tetrazolyl.

The term "$C_1$-$C_{10}$ alkyl" refers to the straight and branched aliphatic radicals of 1 to 10 carbon atoms such as methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl), tert-octyl (1,1,3,3-tetramethylbutyl), nonyl, 1-, 2-, 3-, 4-, 5-, 6-, or 7-methyloctyl, 1-, 2-, 3-, 4-, or 5-ethylheptyl, 1-, 2-, or 3-propylhexyl, decyl, 1-, 2-, 3-, 4-, 5-, 6-, 7-, or 8-methylnonyl, 1-, 2-, 3-, 4-, 5-, or 6-ethyloctyl, 1-, 2-, 3-, or 4-propylheptyl, and the like. The term "$C_1$-$C_{10}$ alkyl" includes within its definition the terms "$C_1$-$C_3$ alkyl", "$C_1$-$C_4$ alkyl", and "$C_1$-$C_6$ alkyl".

The term "$C_3$-$C_8$ cycloalkyl" refers to the saturated alicyclic rings of three to eight carbon atoms such as cyclopropyl, methylcyclopropyl, cyclobutyl, cyclopentyl, cyclohexyl, cyclooctyl, and the like.

The term "$C_2$-$C_6$ alkenyl" refers to straight and branched radicals of two to six carbon atoms such as ethenyl, allyl, isopropenyl, butenyl, isobutenyl, 3-methyl-2-butenyl, n-hexenyl, and the like.

The term "halo" refers to fluoro, chloro, bromo, and iodo. The term "$C_1$-$C_4$ alkoxy" refers to straight and branched alkoxy radicals of up to four carbon atoms, such as methoxy, ethoxy, n-propoxy, isopropoxy, n-butoxy, tert-butoxy, and the like.

The term "A" can refer to straight and branched chain "$C_1$-$C_{10}$ alkylidenes" such as —CH$_2$—, —CH(CH$_3$)—, —C(CHH$_3$)$_2$—, —CH(C$_2$H$_5$)—, —CH$_2$CH$_2$—, —CH$_2$CH(CH$_3$)—, —CH(CH$_3$)CH$_2$—, —CH(CH$_3$)CH(CH$_3$)—, —CH$_2$C(CH$_3$)$_2$—, —CH$_2$CH(C$_2$H$_5$)—, —CH$_2$CH$_2$CH$_2$—, —CH(CH$_3$)CH$_2$CH$_2$—, —CH$_2$CH(CH$_3$)CH$_2$—, —CH$_2$CH(C$_2$H$_5$)CH$_2$—, —CH$_2$CH$_2$CH(C$_2$H$_5$)—, —C(CH$_3$)$_2$CH$_2$CH$_2$—, —CH(CH$_3$)CH$_2$CH(CH$_3$)—, —CH$_2$CH$_2$CH$_2$CH$_2$—, —CH$_2$C(CH$_3$)$_2$CH$_2$CH$_2$—, —CH$_2$C(CH$_3$)$_2$CH$_2$—, —CH$_2$CH$_2$CH(C$_2$H$_5$)CH$_2$—, —CH$_2$CH$_2$CH$_2$CH$_2$CH$_2$—, —CH(CH$_3$)CH$_2$CH$_2$CH$_2$CH$_2$—, —CH$_2$CH$_2$CH$_2$CH$_2$CH$_2$CH$_2$—, —(CH$_2$)$_{10}$—, and the like.

Similarly, a "$C_2$-$C_4$ alkenylidene" group refers to moieties such as —CH=CH—, —C(CH$_3$)=CH—, —C(CH$_3$)=C(CH$_3$)—, —CH(C$_2$H$_5$)=CH—, —CH=CH—CH$_2$—, —C(CH$_3$)=CH—CH$_2$—, —CH=C(CH$_3$)—CH$_2$—, —CH=CH—CH(CH$_3$)—, —CH=CH—CH$_2$CH$_2$—, —CH$_2$—CH=CH—CH$_2$—, and the like.

The term "cyclic $C_5$-$C_{10}$ alkylidene" refers to five to ten membered carbon alkylidines having a carbocyclic cyclic group between two methylene groups, such as

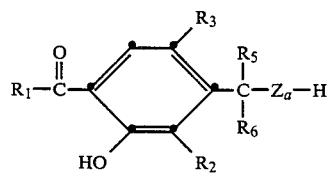

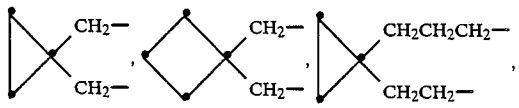

and the like.

The definition of —A—Q—A—Y— of a cyclic substructure when added to two carbon atoms of the phenyl ring provides a bicyclic moiety such as an α-tetralone (where E is —CH$_2$—), indanone (E is a bond), 4-chromanone (E is —O—) or thiochroman-4-one (E is —S—). The bicyclic group can be attached to at any of the otherwise unsubstituted carbon atoms of the phenyl ring and the —A—R$_4$ substituent may be attached at any of the two or three remaining carbon atoms of the ketone-containing ring.

The pharmaceutically acceptable base addition salts of this invention include salts derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine, and the like. The potassium and sodium salt forms are particularly preferred.

It is recognized that if R$_5$ is different from R$_6$, when alkyl or alkylidene groups are branched, etc., various stereoisomers will exist This invention is not limited to any particular stereoisomer but includes all possible individual isomers and racemates of the compounds of Formula I. Similarly, when alkene or alkenylidene groups are present, both the individual cis and trans isomers and their mixture are included as part of this invention.

Some of the compounds of this invention may be prepared by the reaction of a compound of the Formula II

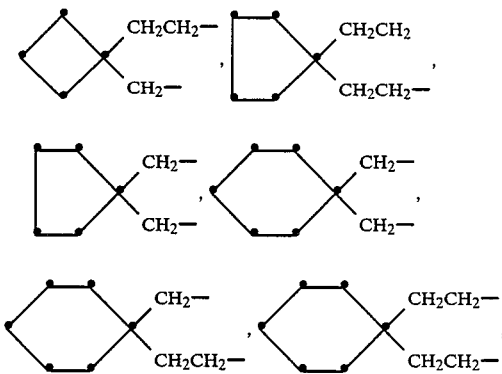

wherein Z$_a$ is —O—, —NR—, or —S—, with a compound of the formula III

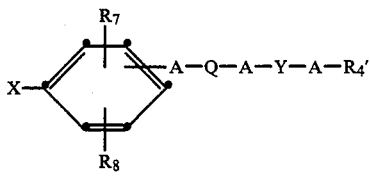

wherein X is a suitable leaving group, such as halo, preferably chloro, and $R_4'$ is $R_4$, cyano, bromo, iodo, or chloro. This procedure is useful in preparing the compounds of this invention designated by Formula I'

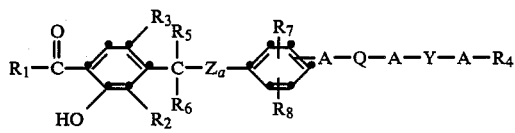

either directly (when $R_4'$ is $R_4$) or indirectly from intermediates IV

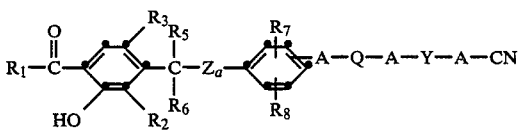

The reaction between compounds II and III is usually performed employing equimolar amounts although ratios other than equimolar amounts are completely operative. The reaction is best carried out in a non-reactive solvent such as ketones, especially acetone or methyl ethyl ketone, or dimethylformamide, and in the presence of a base, preferably an alkali metal hydroxide or carbonate, preferably potassium carbonate. Especially when X is chloro, a catalyst such as potassium or sodium iodide may be added to increase the reaction rate. The reaction may be carried out at temperatures of about ambient temperature up to the boiling point of the reaction mixture, the latter being preferred.

In the case where $R_4'$ is cyano, the resulting intermediate IV may be converted to the compounds of this invention by the following methods. Compounds of Formula I' wherein $R_4$ is —COOH may be obtained by hydrolysis of the intermediate cyano derivative. This is generally accomplished by heating the cyano derivative in aqueous alcohol in the presence of a base such as sodium hydroxide. Alternatively, the carboxylic acid derivatives (I', $R_4$ is —COOH) may be prepared by the aqueous hydrolysis of the corresponding ester derivatives as described above. The compounds of Formula I' wherein $R_4$ is —COO($C_1$-$C_4$ alkyl) may be prepared by conventional methods of esterification from the respective acid derivatives or are prepared directly by the methods described below. Salts may be prepared by treating the corresponding acids ($R_4$ is —COOH) with an appropriate base in the normal manner.

The compounds of Formula I' wherein $R_4$ is 5-tetrazolyl are prepared by treating the cyano intermediate of formula IV with an alkali metal azide such as sodium azide, ammonium chloride, and (optionally) lithium chloride in a non-reactive high-boiling solvent such as N,N-dimethylformamide (DMF), preferably at temperatures from about 60° C. to about 125° C. Alternatively, tri-n-butyltin azide or tetramethylguanidinium azide, in a solvent such as tetrahydrofuran, dimethoxyethane, diethoxyethane, or the like, may be used in place of the alkali metal azide, ammonium chloride, lithium chloride and DMF. The tetrazole functionality of $R_4$ can be introduced from the corresponding nitrile precursor either in the beginning of, in the middle of, or preferably at the end of the other chemical transformations. Thus, it is preferred that the tetrazole functionality be introduced from the corresponding cyano group as one of the last, if not the last, step of the chemical sequence.

When employing intermediate III wherein $R_4'$ is iodo, bromo, or chloro, those skilled in the art will recognize that dihaloalkane III is non-symmetrically substituted. Those skilled in the art will also recognize that X should be a better leaving group than $R_4'$ in order for the desired product IV to be formed. If $R_4'$ is the better leaving group in compound III, III can first be converted to a different intermediate III (e.g., reaction of III ($R_4'$ is iodo, bromo, or chloro) with an alkali metal cyanide to give III (where $R_4'$ is —CN)) which can then be reacted with compound II as previously described.

The compounds of Formula IV wherein $R_4'$ is bromo, iodo, or chloro may be transformed into the compounds of this invention in the following manner. When compounds of Formula IV ($R_4'$ is iodo, bromo, or chloro) are heated with an alkali metal cyanide, such as sodium cyanide, in the presence of a high boiling, nonreactive solvent, such as N,N-dimethylformamide, at elevated temperatures (50° C. to the reflux temperature of the solvent), the intermediate cyano compound of Formula IV ($R_4'$ is cyano) is produced which may then be transformed into the acid, ester, or tetrazole derivatives as described previously.

Alternatively, nitrile intermediate IV can be prepared from the corresponding ester upon treatment with sodium metal in liquid ammonia. For example, treatment of the esters under these conditions in the presence of acetonitrile and a catalytic amount of ferric chloride produces a 3-oxopropionitrile which can be transformed into the acid, ester, or tetrazole as described above. Nitriles can also be prepared by converting the corresponding carboxylic acid to a carboxamide by standard techniques (e.g., first treating with methanesulfonyl chloride followed by ammonia) and dehydrating the unsubstituted amide with agents such as phosphorous pentoxide, phosphorous pentachloride, or preferably methanesulfonyl chloride.

A preferred process for preparing I' is that of reacting the appropriate benzyl derivative VI

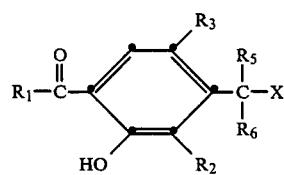

with a derivative of Formula VII

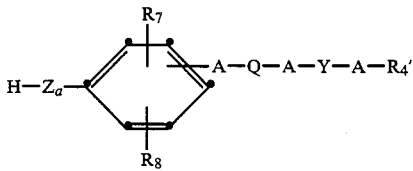

to give compounds I' directly or indirectly through intermediate IV.

Other compounds of Formula I' are prepared directly or indirectly by treating a bromo-compound of the Formula VIII

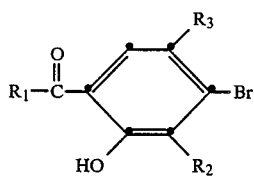

with a strong base, such as lithium diisopropylamide, in an inert solvent, such as diethyl ether, at low temperatures, preferably −20° to 0° C., to prepare the lithium salt of VIII which is then reacted with III'

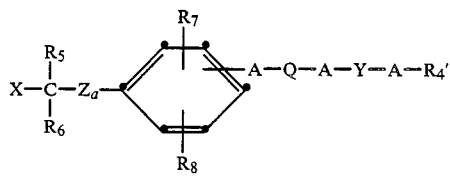

to provide compounds I directly (when $R_4'$ is $R_4$) or intermediates IV.

The thio derivatives and intermediates of this invention (p is 0) may be transformed into the corresponding sulfoxide (p is 1) compounds upon treatment with a mild oxidizing agent, such as hydrogen peroxide in methanol or an alkali metal periodate in aqueous alcohol. The corresponding sulfones (p is 2) are prepared from the thio or sulfoxide compounds on treatment with a strong oxidizing agent such as hydrogen peroxide in acetic acid or m-chloroperbenzoic acid in methanol.

The 2-thioxo-4-thiazolidinones of this invention may be prepared by condensing an intermediate, such as III, I, VII, or the like, where $R_4$ or $R_4'$ is —CHO, with rhodanine, usually by heating with fused sodium acetate and acetic acid, followed by reduction, such as catalytic hydrogenation, of the resulting ethylene intermediate. These transformations are well known in the art.

Similarly, the 3-(1,2,5-thiadiazoles) of this invention can be prepared by reacting intermediates corresponding to III, I', VII, and the like where $R_4$ or $R_4'$ is —CH($NH_2$)$CONH_2$ with N-methyl-N-(trimethylsilyl)-trifluoroacetamide and thionyl chloride. Once again, the preparation and transformation of such amino acid related intermediates are known to skilled artisans.

In addition, various compounds of Formula I can be prepared from other compounds, precursors, or intermediates of Formula I by standard methods such as hydrolysis, esterification, alkylation, oxidation, reduction, aminolysis, halogenation, and the like, as are well known to those skilled in the art.

Intermediate compounds II, VI, and IX are disclosed in EPO publication No. 132,366 which is expressly incorporated into this application by reference. This publication also provides general methods of reacting such intermediates in the same manner as provided above.

Other intermediates required to prepare the compounds of this invention are either commercially available, known in the literature, or can be prepared according to methods known in the art.

For example, many of the preferred acids and esters of Formula Ia are prepared from intermediate XV.

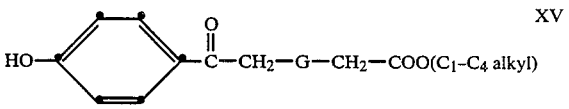

where G is a bond or $C_1$-$C_3$ alkylidene. Compounds of Formula XV can be prepared by acylating anisole with an anhydride of Formula XVI

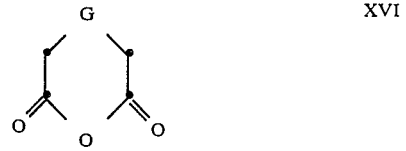

to provide intermediate XVII

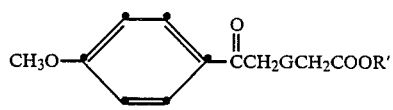

where R' is hydrogen. The acylation is generally carried out under standard Friedel-Crafts conditions in the presence of a Lewis acid. A slight molar excess of anhydride is preferably employed. The reaction is preferably carried out in the presence of a non-reactive solvent, such as dichloromethane, and the preferred Lewis acid is aluminum chloride. Alternatively, anisole can be acylated with $ClOCCH_2GCH_2COO(C_1$-$C_4$ alkyl) under the same conditions to provide XVII where R' is $C_1$-$C_4$ alkyl.

Compounds of Formula XVII can then be transformed into the corresponding phenols upon treatment with standard demethylating reagents. Useful reagents include refluxing 48% hydrobromic acid in acetic acid. Such conditions also serve to hydrolyze the ester to the carboxylic acid. Reesterification by standard techniques, such as heating the acid at reflux in the appropriate alcohol in the presence of a catalytic amount of an acid, such as sulfuric acid or methanesulfonic acid, provides the intermediate of Formula XV.

Another alternate method of preparing compounds such as those provided by Formula Ia involves the acylation of a 4-unsubstituted phenyl derivative as provided by the following scheme:

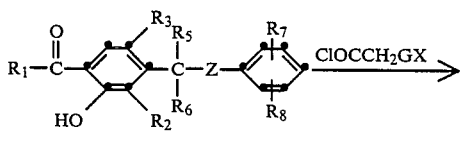

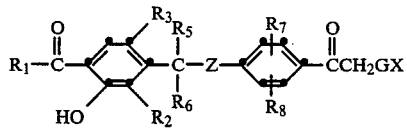

XIX

Acylation of XVIII by standard conditions as described above with ClOCCH$_2$GX provide intermediate XIX which can be transformed into the corresponding nitrile by methods analogous to those provided above. The nitrile can then be converted into a compound of the invention by previously described methods. Formation of XVIII is accomplished by methods described above employing the appropriate nonacylated phenyl derivative.

The compounds of this invention where Q=CHOH can be obtained from the corresponding ketones (Q=C=O) by reduction with sodium borohydride in methanol or ethanol. The reduction step is preferably performed on final compounds I' or intermediates IV followed by the remaining transformations.

As is well known in the art, the R$_3$ chloro and bromo derivatives may be prepared by halogenation of the corresponding hydrogen compounds (R$_3$ is hydrogen) of this invention (I) or of the corresponding intermediates followed by other transformations as desired.

The following preparations and examples further illustrate the preparation of the starting materials, intermediates, and compounds of this invention. The examples are illustrative only and are not intended to limit the scope of the invention. Where structures were confirmed by infra-red or proton nuclear magnetic resonance analysis, the compound is so designated by "IR" and/or "NMR", respectively.

EXAMPLE 1

4-[(4-Acetyl-3-hydroxy-2-propylphenyl)methoxy]-γ-oxobenzenebutanoic acid

A. Preparation of 4-(4-methoxyphenyl)-4-oxobutanoic acid.

To a solution of 200 g. of anisole in 2 L. of methylene chloride were added 278 g. of succinic anhydride. The mixture was cooled by means of an external ice bath and 492.2 g. of aluminum chloride were added in portions with stirring. The reaction was kept cool an additional several hours and then allowed to come to room temperature overnight. The mixture was poured into a mixture of ice and hydrochloric acid. The white precipitate which formed was recovered by vacuum filtration. The solid was dried and then dissolved in 5N sodium hydroxide. The solution was filtered and made acidic with hydrochloric acid. The resulting precipitate was extracted with ethyl actate. The layers were separated and the organic layer was dried over sodium sulfate/magnesium sulfate, filtered, and evaporated in vacuo. The residue was crystallized from ethanol providing 240.1 g. of the desired subtitle intermediate, m.p. 142°–144° C.

Analysis for C$_{11}$H$_{12}$O$_4$: Calculated: C, 63.45; H, 5.81; Found: C, 63.57; H, 5.69.

B. Preparation of ethyl 4-(4-hydroxyphenyl)-4-oxobutanoate.

A mixture of 100 g. of 4-(4-methoxyphenyl)-4-oxobutanoic acid, 500 ml. of 48% hydrobromic acid, and 1000 ml. of acetic acid were heated at reflux for 36 hours. The reaction mixture was concentrated in vacuo and ethanol was added. Crystallization from 9:1 toluene/ethyl acetate provided 69.1 g. of the desired subtitle intermediate. MS, NMR.

C. Preparation of 4-[(4-acetyl-3-hydroxy-2-propylphenyl)methoxy]-γ-oxobenzenebutanoic acid, ethyl ester.

To 200 ml. of absolute ethanol were added 1.38 g. of sodium metal. After dissolution was complete, 16.6 g. of the intermediate from Example 1B above were added followed by the addition of 11.4 g. of 4-acetyl-3-hydroxy-2-propylbenzyl chloride and 7.5 g. of sodium iodide. The reaction mixture was stirred under a nitrogen atmosphere for approximately 72 hours. The solution was poured into water and filtered. The solids were dried and provided 19.7 g. of the desired subtitle ester, m.p. 125°–127° C. MS, NMR.

D. Preparation of 4-[(4-acetyl-3-hydroxy-2-propylphenyl)methoxy]-γ-oxobenzenebutanoic acid.

To a mixture of 19.7 g. of the ester from Example 1C above and 250 ml. of ethanol were added 30 ml. of 5N sodium hydroxide. The mixture was heated at reflux for 2 hours, poured into water, and made acidic with concentrated hydrochloric acid. The resulting precipitate was recovered by vacuum filtration. Crystallization from ethanol provided 12.4 g. of the desired title product, m.p. 175°–176° C.

Analysis for C$_{22}$H$_{24}$O$_6$. Calculated: C, 68.74; H, 6.29; Found: C, 68.96; H, 6.07.

EXAMPLES 2–4

The following compounds were prepared from the appropriate phenol following the procedure of Example 1C.

2. 4-[(4-Acetyl-3-hydroxy-2-propylphenyl)methoxy]-ε-soxobenzenehexanoic acid, ethyl ester. 82% yield, m.p. 97°–98° C.

Analysis for C$_{26}$H$_{30}$O$_6$: Calculated: C, 71.21; H, 6.90; Found: C, 70.99; H, 6.72.

3. 4-[(4-Acetyl-3-hydroxy-2-propylphenyl)methoxy]-β,β-dimethyl-δ-oxobenzenepentanoic acid, ethyl ester, 63% yield, m.p. 74°–78° C.

Analysis for C$_{27}$H$_{34}$O$_6$: Calculated: C, 71.34; H, 7.54; Found: C, 71.22; H, 7.63.

4. 4-[(4-Acetyl-3-hydroxy-2-propylphenyl)methoxy]-δ-oxobenzenepentanoic acid, ethyl ester, 95% yield, m.p. 61°–62° C.

Analysis for C$_{25}$H$_{30}$O$_6$: Calculated: C, 70.40; H, 7.09; Found: C, 70.36; H, 7.11.

EXAMPLES 5–7

The following compounds were prepared from corresponding esters of Examples 2–4 following the procedure of Example 1D.

5. 4-[(4-Acetyl-3-hydroxy-2-propylphenyl)methoxy]-ε-oxobenzenehexanoic acid, 56% yield, m.p. 118°–119° C.

Analysis for C$_{24}$H$_{28}$O$_6$: Calculated: C, 69.89; H, 6.84; Found: C, 70.10; H, 6.77.

6. 4-[(4-Acetyl-3-hydroxy-2-propylphenyl)methoxy]-β,β-dimethyl-δ-oxobenzenepentanoic acid, 13% yield, m.p. 99°–100° C.

Analysis for C$_{25}$H$_{30}$O$_6$: Calculated: C, 70.40: H, 7.09; Found: C, 70.67; H, 7.20.

7. 4-[(4-Acetyl-3-hydroxy-2-propylphenyl)methoxy]-δ-oxobenzenepentanoic acid, 61% yield, m.p. 127°–128° C.

Analysis for $C_{23}H_{26}O_6$: Calculated: C, 69.33; H, 6.58; Found: C, 69.47; H, 6.54.

EXAMPLE 8

1-{4-[(4-acetyl-3-hydroxy-2-propylphenyl)methoxy]-phenyl}-2-(1H-tetrazol-5-yl)ethanone A. Preparation of 4-[(4-acetyl-3-hydroxy-2-propylphenyl)methoxy]benzoic acid, ethyl ester.

Following the procedure of Example 1C, 2.9 g. of 4-acetyl-3-hydroxy-2-propylbenzyl chloride and 4.5 g. of 4-hydroxybenzoic acid, ethyl ester were allowed to react and provided 4.6 g. of the subtitle intermediate, m.p. 70°–72° C.

Analysis for $C_{21}H_{24}O_5$: Calculated: C, 70.76; H, 6.78; Found: C, 69.98; H, 6.78.

B. Preparation of 4-[(4-acetyl-3-hydroxy-2-propylphenyl)methoxy]-β-oxobenzenepropionitrile.

To 250 ml. of liquified ammonia approximately −30° C. were added 0.48 g. of sodium metal and a trace amount of ferric chloride. Under a nitrogen atmosphere, 3.0 g. of acetonitrile and 2.5 g. of the ester from Example 8A were added in 25 ml. diethyl ether. After stirring for 3 hours at room temperature, diethyl ether was added and the ammonia was allowed to evaporate. Water was added and the layers were separated. The aqueous layer was acidified and extracted with ethyl acetate. The ethyl acetate layers were combined, dried over sodium sulfate, and concentrated in vacuo. The residue was purified by high pressure liquid chromatography over silica gel eluting with 9:1 toluene/ethyl acetate. The appropriate fractions were combined and evaporated to provide 0.4 g. of the desired subtitle nitrile, m.p. 164°–166° C.

Analysis for $C_{21}H_{21}NO_4$: Calculated: C, 72.84; H, 6.24; N, 4.14; Found: C, 73.58; H, 5.64; N, 3.73.

C. Preparation of 1-{4-[(4-acetyl-3-hydroxy-2-propylphenyl)methoxy]phenyl}-2-(1H-tetrazol-5-yl)ethanone.

A mixture of 2 g. of the nitrile from Example 8B and 6.6 g. of tri-n-butyltin azide were heated at reflux for 4 days in 1,2-dimethoxyethane. After cooling, the mixture was poured into a mixture of 150 ml. of ice and 50 ml. of hydrochloric acid. After stirring for 1 hour, the resulting precipitate was recovered by filtration. The solid was dissolved in ethyl acetate. Crystallization was induced by adding hexane and after cooling for several days, the resulting crystals were ecovered by filtration providing 1.0 g. of the desired title product, m.p. 207°–209° C.

Analysis for $C_{21}H_{22}N_4O_4$: Calculated: C, 63.94; H, 5.62; N, 14.21; Found: C, 64.35; H, 5.51; N, 14.00.

EXAMPLES 9–19

The following tetrazoles were prepared from corresponding nitrile intermediates according to the procedure of Example 8C.

9. 1-{4-[(4-Acetyl-3-hydroxy-2-propylphenyl)methoxy]phenyl}-3-(1H-tetrazol-5-yl)-1-propanone, 16% yield, m.p. 206°–208° C.

Analysis for $C_{22}H_{24}N_4O_4$: Calculated: C, 64.69; H, 5.92; N, 13.72; Found: C, 64.78; H, 5.89; N, 13.51.

10. 1-{4-[(4-Acetyl-3-hydroxy-2-propylphenyl)methoxy]-phenyl}-4-(1H-tetrazol-5-yl)-1-butanone, 56% yield, m.p. 178°–180° C.

Analysis for $C_{23}H_{26}N_4O_4$: Calculated: C, 65.39; H, 6.20; N, 13.26; Found: C, 65.59; H, 6.10; N, 13.43.

11. 1-{4-[(4-Acetyl-3-hydroxy-2-propylphenyl)methoxy]phenyl}-5-(1H-tetrazol-5-yl)-1-pentanone, 51% yield, m.p. 163°–166° C.

Analysis for $C_{24}H_{28}N_4O_4$: Calculated: C, 66.04; H, 6.47; N, 12.84; Found: C, 66.29; H, 6.34; N, 12.64.

12. 1-{4-[(4-Acetyl-3-hydroxy-2-propylphenyl)methoxy]phenyl}-2,2-dimethyl-3-(1H-tetrazol-5-yl)-1-propanone, 31% yield, m.p. 44°–50° C.

Analysis for $C_{24}H_{28}N_4O_4$: Calculated: C, 66.04; H, 6.47; N, 12.84; Found: C, 65.90; H, 6.65; N, 12.59.

13. 1-{4-[(4-Acetyl-3-hydroxy-2-propylphenyl)methoxy]-2-hydroxyphenyl}-4-(1H-tetrazol-5-yl)-1-butanone, 32% yield, m.p. 170°–174° C.

Analysis for $C_{23}H_{21}N_4O_5$: Calculated: C, 63.00; H, 5.98; N, 12.78; Found: C, 63.04; H, 6.22; N, 12.55.

14. 1-{4-[(4-Acetyl-3-hydroxy-2-propylphenyl)methoxy]phenyl}-2-methyl-3-(1H-tetrazol-5-yl)-1-propanone, 41% yield, m.p. 140°–142° C.

Analysis for $C_{23}H_{26}N_4O_4$: Calculated: C, 65.39; H, 6.20; N, 13.26; Found: C, 65.56; H, 6.03; N, 12.98.

15. 1-{4-[(4-Acetyl-3-hydroxy-2-propylphenyl)methoxy]phenyl}-3,3-dimethyl-4-(1H-tetrazol-5-yl)-1-butanone, 31% yield, m.p. 151°–153° C.

Analysis for $C_{25}H_{30}N_4O_4$: Calculated: C, 66.65; H, 6.71; N, 12.44; Found: C, 66.79; H, 6.85; N, 12.26.

16. 1-{4-[(4-Acetyl-3-hydroxy-2-ethylphenyl)methoxy]phenyl}-3,3-dimethyl-4-(1H-tetrazol-5-yl)-1-butanone, 41% yield, m.p. 121°–123° C.

Analysis for $C_{24}H_{28}N_4O_4$: Calculated: C, 66.04; H, 6.47; N, 12.84; Found: C, 66.62; H, 6.72; N, 12.51.

17. 1-{4-[(4-Acetyl-3-hydroxy-2-propylphenyl)methoxy]phenyl}-4-methyl-4-(1H-tetrazol-5-yl)-1-pentanone, 60% yield, m.p. 153°–158° C.

Analysis for $C_{25}H_{30}N_4O_4$: Calculated: C, 66.65; H, 6.71; N, 12.44; Found: C, 66.36; H, 6.79; N, 12.24.

18. 1-{3-[(4-Acetyl-3-hydroxy-2-propylphenyl)methoxy]phenyl}-4-(1H-tetrazol-5-yl)-1-butanone, 57% yield, m.p. 140°–145° C.

Analysis for $C_{23}H_{26}N_4O_4$: Calculated: C, 65.39; H, 6.20; N, 13.26; Found: C, 65.17; H, 6.39; N, 12.97.

19. 1-{4-[(4-Acetyl-3-hydroxy-2-propylphenyl)methoxy]phenyl}-6-(1H-tetrazol-5-yl)-1-hexanone, 66% yield, m.p. 135°–138° C.

Analysis for $C_{25}H_{30}N_4O_5$: Calculated: C, 66.65: H, 6.71: N, 12.44: Found: C, 67.62 H, 7.14: N, 12.40.

EXAMPLES 20–22

The following compounds were prepared from the appropriate phenols according to the procedure of Example 1C.

20. 4-[(4-Acetyl-2-ethyl-3-hydroxyphenyl)methoxy]β,β-dimethyl-δ-oxobenzenepentanoic acid, ethyl ester, 80% yield, m.p. 93°–97° C.

Analysis for $C_{26}H_{32}O_6$: Calculated: C, 70.89; H, 7.32; Found: C, 70.96; H, 7.42.

21. 1-(2-{4-[(4-Acetyl-3-hydroxy-2-propylphenyl)methoxy]phenyl}-2-oxoethyl)cyclopentaneacetic acid, ethyl ester, 96% yield, m.p. 94°–95° C.

Analysis for $C_{29}H_{36}O_6$: Calculated: C, 72.48; H, 7.55; Found: C, 72.75; H, 7.63.

22. 4-[(4-Acetyl-3-hydroxy-2-propylphenyl)methoxy]-β-methyl-β-ethyl-δ-oxobenzenepentanoic acid, ethyl ester, 73% yield, oil.

Analysis for $C_{28}H_{36}O_6$: Calculated: C, 71.03; H, 7.95; Found: C, 71.06; H, 7.81.

EXAMPLES 23-25

The following compounds were prepared by hydrolysis of the corresponding esters according to the procedure of Example 10.

23. 4-[(4-Acetyl-2-ethyl-3-hydroxyphenyl)methoxy]-$\beta,\beta$-dimethyl-$\delta$-oxobenzenepentanoic acid, 80% yield, m.p. 120°-122° C.

Analysis for $C_{24}H_{28}O_6$: Calculated: C, 69.89 H, 6.84; Found: C, 69.79 H, 6.94.

24. 1-(2-{4-[(4-Acetyl-3-hydroxy-2-propylphenyl)methoxy]phenyl}-2-oxoethyl)cyclopentaneacetic acid, 61% yield, m.p. 103°-104° C.

Analysis for $C_{27}H_{32}O_6$: Calculated: C, 71.66; H, 7.13; Found: C, 71.76; H, 7.34.

25. 4-[(4-Acetyl-3-hydroxy-2-propylphenyl)methoxy]-$\beta$-methyl-$\beta$-ethyl-$\delta$-oxobenzenepentanoic acid, 61% yield, m.p. 52°-60° C.

Analysis for $C_{26}H_{32}O_6$: Calculated: C, 70.89; H, 7.32; Found: C, 71.26; H, 7.73.

EXAMPLE 26

6-[(4-Acetyl-3-hydroxy-2-propylphenyl)methoxy]-1,2,3,4-tetrahydro-1-oxo-2-naphthaleneacetic acid, ethyl ester A. Preparation of 6-methoxy-1,2,3,4-tetrahydro-1-oxo-2-naphthaleneacetic acid, ethyl ester.

A 1.6M solution of n-butyllithium in hexane (262.5 ml.) was slowly added to a chilled solution of 58.8 ml. of diisopropylamine in 260 ml. of tetrahydrofuran. After stirring for 30 minutes, the solution was added to a solution of 71.3 g. of 6-methoxy-1-tetralone in 300 ml. of tetrahydrofuran and 200 ml. of hexamethylphosphoramide previously cooled to −60° to −70° C. After stirring for one hour, 46.6 ml. of ethyl bromoacetate were added over a 90 minute period.

After stirring at −60° C. for 3 hours, the cooling bath was removed and the reaction stirred an additional 20 hours. The solvents were removed in vacuo and the residue dissolved in ethyl acetate. The organic solution was washed with water, dried over magnesium sulfate, and concentrated in vacuo. The residue was vacuum distilled. The fraction collected at 135°-152° C. and 0.04 torr provided 36.6 g. of the desired subtitle intermediate.

Analysis for $C_{15}H_{18}O_4$: Calculated: C, 68.69; H, 6.92; Found: C, 68.37; H, 6.83.

B. Preparation of 6-hydroxy-1,2,3,4-tetrahydro-1-oxo-2-naphthaleneacetic acid, ethyl ester.

Fifty-seven grams of 6-methoxy-1,2,3,4-tetrahydro-1-oxo-2-naphthaleneacetic acid, ethyl ester were heated to reflux in one liter of methylene chloride with 87.1 g. of aluminum chloride. After 48 hours, 50 additional grams of aluminum chloride were added. After additional stirring, the mixture was poured into ice, methylene chloride, and ethyl acetate. The layers were separated, and the organic layer was washed with dilute hydrochloric acid, dried over magnesium sulfate, and concentrated in vacuo. The residue was dissolved in 200 ml. of ethanol, 20 ml. of methanesulfonic acid added, and the mixture stirred for 24 hours. The solution was poured into water, extracted with ethyl acetate, and the organic solution was washed with a sodium bicarbonate solution, dried over magnesium sulfate, and concentrated in vacuo to provide 18 g. of the desired subtitle intermediate.

Analysis for $C_{14}H_{16}O_4$: Calculated: C, 67.73; H, 6.50; Found: C, 67.94; H, 6.38.

C. Preparation of 6-[(4-acetyl-3-hydroxy-2-propylphenyl)methoxy]-1,2,3,4-tetrahydro-1-oxo-2-naphthaleneacetic acid, ethyl ester The title product was prepared in 76% yield from the phenol of Example 26B according to the procedure of Example 1C—potassium t-butoxide was employed in place of sodium metal.

Analysis for $C_{26}H_{30}O_6$: Calculated: C, 71.21: H, 6.90: Found: C, 71.09: H, 7.00.

EXAMPLE 27

7-[(4-Acetyl-3-hydroxy-2-propylphenyl)methoxy]-1,2,3,4-tetrahydro-1-oxo-2-naphthaleneacetic acid, ethyl ester The title compound was prepared in 81% yield from 7-hydroxy-1,2,3,4-tetrahydro-1-oxo-2-naphthaleneacetic acid, ethyl ester following the procedure of Example 26C.

EXAMPLES 28-29

The following carboxylic acids were prepared from the corresponding esters following the procedure of Example 1D.

28. 6-[(4-Acetyl-3-hydroxy-2-propylphenyl)methoxy]-1,2,3,4-tetrahydro-1-oxo-2-naphthaleneacetic acid, 43% yield, m.p. 147°-149° C.

Analysis for $C_{24}H_{26}O_6$: Calculated: C, 70.23; H, 6.38; Found: C, 69.96; H, 6.45.

29. 7-[(4-Acetyl-3-hydroxy-2-propylphenyl)methoxy]-1,2,3,4-tetrahydro-1-oxo-2-naphthaleneacetic acid, 64% yield, m.p. 107°-109° C.

Analysis for $C_{24}H_{26}O_6$: Calculated: C, 70.23; H, 6.38; Found: C, 71.58; H, 6.72.

EXAMPLE 30

1-{4-[(4-Acetyl-3-hydroxy-2-propylphenyl)methoxy]phenyl}-7-(1H-tetrazol-5-yl)-1-heptanone The title product was prepared in 22% yield from the corresponding nitrile intermediate following the procedure of Example 8C, m.p. 134°-137° C.

Analysis for $C_{26}H_{32}N_4O_4$: Calculated: C, 67.22; H, 6.94; N, 12.06; Found: C, 67.49; H, 7.18; N, 12.27.

The compounds of Formula I should be useful in treating any condition, including clinical conditions, which is characterized by excessive release of leukotrienes $C_4$, $D_4$, or $E_4$. These conditions include immediate type hypersensitivity reactions such as asthma. Evidence obtained over the past few years has shown the presence of leukotrienes in sputum of patients with chronic bronchitis (Turnbull, et al., *Lancet II*, 526 (1977)) and cystic fibrosis (Cromwell, et al., *Lancet II*, 164 (1981)), suggesting a role of leukotrienes in the pathology of those diseases. Furthermore, Lewis and colleagues [*Int. J. Immunopharmacology*, 4, 85 (1982)] have recently detected material in rheumatoid synovial fluid that reacts antigenically with antibody to $LTD_4$. This may hallmark the existence of leukotriene permeability factors that, together with $LTB_4$, augment the inflammatory process in the diseased joints. Therefore, the compounds described in this invention should also alleviate some of the symptoms of chronic bronchitis and cystic fibrosis and possibly rheumatoid arthritis by virtue of their ability to antagonize leukotrienes. The compounds are also useful for inhibiting the cardiovascular effects of leukotrienes thereby rendering them useful for treating conditions such as shock and ischemic heart disease.

The term "excessive release" of leukotrienes refers to an amount of leukotrienes sufficient to cause the particular condition associated with such amount. The amount of leukotriene which is considered to be excessive will depend on a variety of factors, including the specific leukotriene(s) involved, the amount of leukotriene required to cause the particular condition, and the species of the mammal involved. As will be appreciated by those skilled in the art, the success of treating a mammal suffering from or susceptible to a condition characterized by an excessive release of leukotrienes with a compound of formula I will be measured by the regression or prevention of the symptoms of the condition. The bicyclic compounds of this invention provide exceptionally high blood levels.

Leukotriene antagonism was demonstrated by the following test procedure:

Male, Hartley guinea pigs weighing 200–450 grams were killed by decapitation. A section of terminal ileum was removed, the lumen cleaned, and the tissue divided into 2.5 cm. segments. The ilea were mounted in 10 ml. tissue baths containing Krebs-bicarbonate solution of the following composition in mmoles/liter: KCl, 4.6; $CaCl_2 \cdot H_2O$, 1.2; $KH_2PO_4$, 1.2; $MgSO_4 \cdot 7H_2O$, 1.2; NaCl, 118.2; $NaHCO_3$, 24.8; and dextrose, 10.0. The bath fluid was maintained at 37° C. and aerated with 95 percent oxygen and 5 percent $CO_2$. In addition, the buffer contained $1 \times 10^{-6}M$ atropine to reduce ileal spontaneous activity. Isometric measurements were made with a Grass FTO3C force-displacement transducer and recorded on a Gras polygraph as change in grams of force. A passive force of 0.5 g. was applied to the tissues. After an appropriate equilibration period, single submaximal control responses to pure $LTD_4$ were obtained. Following a five minute exposure of the ileum to an experimental drug, the control concentration of $LTD_4$ was added to the tissue bath. The response of the ileum to $LTD_4$ in the presence of the drug was compared to the response in the absence of the drug. Various degrees of $LTD_4$ antagonism were obtained using 2–4 different concentrations of an experimental compound on a single ileum. The antagonist concentration that produced 50% inhibition of the $LTD_4$ responses ($-\log IC_{50}$) was interpolated from these data using linear regression.

The testing of the compounds of Formula I in these two procedures is summarized in Table I.

TABLE I

| Compound of Example No. | Percent inhibition of $LTD_4$ evoked ileal contractions |||||  |
|---|---|---|---|---|---|---|
| | Compound Concentration ||||| |
| | $3 \times 10^{-7} M$ | $1 \times 10^{-7} M$ | $3 \times 10^{-8} M$ | $1 \times 10^{-8} M$ | $3 \times 10^{-9} M$ | $-\log IC_{50}$ |
| 1  | 97 |    | 48 |    |    | 7.48 |
| 5  |    | 86 | 63 | 40 |    | 7.80 |
| 6  |    | 78 |    | 41 | 16 | 7.73 |
| 7  |    | 68 |    | 17 |    | 7.43 |
| 8  |    |    | 54 | 40 |    | 7.66 |
| 9  | 91 | 85 | 54 | 25 |    | 7.58 |
| 10 | 94 | 95 | 76 | 57 | 46 | 8.32 |
| 11 |    |    | 51 | 43 |    | 7.61 |
| 12 | 60 |    | 41 |    |    | 7.29 |
| 13 | 82 |    |    | 28 |    | 7.61 |
| 14 |    |    | 58 | 35 |    | 7.69 |
| 15 |    |    | 91 |    | 50 | 8.49 |
| 16 |    | 95 |    | 63 | 41 | 8.32 |
| 18 |    | 84 | 65 | 34 |    | 7.74 |
| 19 |    | 80 | 47 |    |    | 7.49 |
| 23 |    | 88 | 66 | 25 |    | 7.67 |
| 24 |    | 85 | 74 | 35 |    | 7.87 |
| 28 |    |    |    |    |    | 7.99 |
| 29 |    |    |    |    |    | 7.12 |

The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to 500 mg. (from about 5 to 50 mg. in the case of parenteral or inhalation administration, and from about 25 to 500 mg. in the case of oral or rectal administration) of a compound of Formula I. Dosages of from about 0.5 to 300 mg./kg. per day, preferably 0.5 to 20 mg./kg., of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semisolid or liquid material which serves as a vehicle, excipient or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylatedesters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

The following formulation examples may employ as active compounds any of the compounds of this invention. The examples are illustrative only and are not intended to limit the scope of the invention in any way.

EXAMPLE 31

Hard gelatin capsules are prepared using the following ingredients:

| | Quantity (mg./capsule) |
| --- | --- |
| 1-{4-[(4-Acetyl-3-hydroxy-2-propylphenyl)methoxy]phenyl}-4-(1H-tetrazol-5-yl)-1-butanone sodium salt | 250 |
| Starch | 200 |
| Magnesium stearate | 10 |

The above ingredients are mixed and filled into hard gelatin capsules in 460 mg. quantities.

EXAMPLE 32

A tablet is prepared using the ingredients below:

| | Quantity (mg./tablet) |
| --- | --- |
| 1-{4-[(4-Acteyl-3-hydroxy-2-propylphenyl)methoxy]phenyl}-3,3-dimethyl-4-(1H-tetrazol-5-yl)-butanone | 250 |
| Cellulose, microcrystalline | 400 |
| Silicon dioxide, fumed | 10 |
| Magnesium stearate | 5 |

The components are blended and compressed to form tablets each weighing 665 mg.

EXAMPLE 33

An aerosol solution is prepared containing the following components:

| | Weight % |
| --- | --- |
| 4-[(4-Benzoyl-2-allyl-3-hydroxyphenyl)-methoxy]-β-methyl-δ-oxobenzenepentanoic acid ammonium salt | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

EXAMPLE 34

Tablets each containing 60 mg. of active ingredient are made up as follows:

| | |
| --- | --- |
| 1-{4-[(4-Acetyl-3-hydroxy-2-ethyl-phenyl)methoxy]phenyl}-3,3-dimethyl-4-(1H-tetrazol-5-yl)-1-butanone | 60 mg. |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through no. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 35

Capsules each containing 80 mg. of medicament are made as follows:

| | |
| --- | --- |
| 1-(2-{4-[(4-Acetyl-3-hydroxy-2-propylphenyl)methoxy]phenyl}-2-oxoethyl)cyclopentaneacetic acid | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 36

Suppositories each containing 225 mg. of active ingredient are made as follows:

| | |
| --- | --- |
| 1-{4-[(4-propionyl-3-hydroxy-6-methyl-2-propylphenyl)methyl- | |

| | |
|---|---|
| sulfonyl]phenyl}-4-methyl-4-(1H-tetrazol-5-yl)-1-pentanone | 225 mg. |
| Unsaturated or saturated fatty acide glycerides to | 2,000 mg. |

The active ingredient is passed through a No. 60 mesh U.S. sieve and suspended in the fatty acid glycerides previously melted using the minimum heat necessary. The mixture is then poured into a suppository mold of nominal 2 g. capacity and allowed to cool.

EXAMPLE 37

Suspensions each containing 50 mg. of medicament per 5 ml. dose are made as follows:

| | |
|---|---|
| 4-[(4-benzoyl-3-hydroxy-6-chloro-2-allyphenyl)methoxy]-γ-oxobenzene-butanoic acid, methyl ester | 50 mg. |
| Sodium carboxymethyl cellulose | 50 mg. |
| Sugar | 1 g. |
| Methyl paraben | 0.05 mg. |
| Propyl paraben | 0.03 mg. |
| Flavor | q.v. |
| Color | q.v. |
| Purified water to | 5 ml. |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

We claim:

1. A compound of the formula

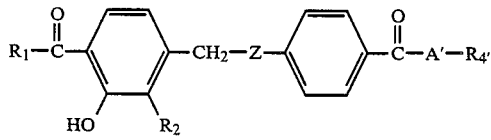

and pharmaceutically acceptable salts thereof, wherein: $R_1$ is $C_1$–$C_6$ alkyl; $R_2$ is $C_1$–$C_6$ alkyl; Z is

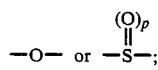

$A'$ is straight or branched chain $C_1$–$C_6$ alkylidene; p is 0, 1, or 2; and $R_4'$ is —COOH or 5-tetrazolyl.

2. A compound of claim 1 wherein $R_1$ is methyl.
3. A compound of claim 2 of the formula

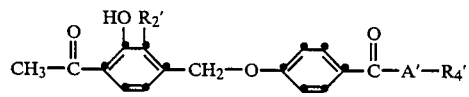
Ia and pharmaceutically acceptable salts thereof wherein:
$R_2'$ is ethyl or propyl; $A'$ is straight or branched chain $C_1$–$C_6$ alkylidene; and
$R_4'$ is —COOH or 5-tetrazolyl.

4. The compound of claim 3 which is 1-{4-[(4-acetyl-3-hydroxy-2-propylphenyl)methoxy]phenyl}-4-(1H-tetrazol-5-yl)-1-butanone or a pharmaceutically acceptable salt thereof.

5. The compound of claim 3 which is 1-{4-[(4-acetyl-3-hydroxy-2-propylphenyl)methoxy]phenyl}-3,3-dimethyl-4-(1H-tetrazol-5-yl)-1-butanone or a pharmaceutically acceptable salt thereof.

6. The compound of claim 3 which is 1-{4-[(4-acetyl-3-hydroxy-2-ethylphenyl)methoxy]phenyl}-3,3-dimethyl-4-(1H-tetrazol-5-yl)-1-butanone or a pharmaceutically acceptable salt thereof.

7. The compound of claim 3 which is 4-[(4-acetyl-3-hydroxy-2-ypropylphenyl)methoxy]-ε-oxobenzenehexanoic acid or a pharmaceutically acceptable salt thereof.

8. The compound of claim 3 which is 4-[(4-acetyl-3-hydroxy-2-propylphenyl)methoxy]-β,β-dimethyl-δ-oxobenzenepentanoic acid or a pharmaceutically acceptable salt thereof.

9. The compound of claim 3 which is 4-[(4-acetyl-2-ethyl-3-hydroxyphenyl)methoxy]-β,β-dimethyl-δ-oxobenzenepentanoic acid or a pharmaceutically acceptable salt thereof.

10. A method of treating a mammal suffering from or susceptible to any condition characterized by an excessive release of leukotrienes, which comprises administering to said mammal a leuktriene antagonizing amount of a compound of claim 1.

11. A method of treating a mammal suffering from or susceptible to any condition characterized by an excessive release of leukotriene, which comprises administering to said mammal a leuktriene antagonizing amount of a compound of claim 3.

12. A method of treating a mammal suffering from or susceptible to an immediate hypersensitivity reaction of the type represented by asthma, which comprises administering to said mammal a therapeutically effective amount of a compound of claim 1.

13. A pharmaceutical formulation comprising a compound of claim 1 in association with a pharmceatically acceptable carrier.

14. A pharmaceutical formuation comprising a compound of claim 3 in association wth a pharmaceutically acceptable carrier 15. A formulation according to claim 14 employing 1-{4-[(4-acetyl-3-hydroxy-2-propylphenyl)methoxy]phenyl}-4-(1H-tetrazol-5-yl)1-butanone or a pharmaceutically acceptable salt thereof.

16. A formulation accordin to claim 14 employing 1-{4-[(4-acetyl-3-hydroxy-2-propylphenyl)methoxy]phenyl}-3,3-dimethyl-4-(1H-tetrazol-5-yl)-1-butanone or a pharmaceutically accepable salt thereof.

17. A formulation according to claim 14 employing 1-{4-[(4-acetyl-3-hydroxy-2-ethylphenyl)methoxy]phenyl}-3,3-dimethyl-4-(1H-tetrazol-5-yl)-1-butanone or a pharmaceutically acceptable salt thereof.

18. A formulation according to claim 14 employing 4-[(4-acetyl-3-hydroxy-2-popylphenyl)methoxy]-ε-oxobenzenehexanoic acid or a pharmceutically acceptable salt thereof.

19. A formulation according to claim 14 employing 4-[(4-acetyl-3-hydroxy-2-propylphenyl)methoxy]-β,β-dimethyl-δ-oxobenzenepentanoic acid or a pharmaceutically acceptable salt thereof.

20. A formulation according to claim 14 employing 4-[(4-acetyl-2-ethyl-3-hydroxyphenyl)methoxy]-β,β-dimethyl-δ-oxobenzenepentanoic acid or a pharmaceutically acceptable salt thereof.

* * * * *